United States Patent
Fadli et al.

(10) Patent No.: US 7,175,670 B2
(45) Date of Patent: Feb. 13, 2007

(54) COUPLERS OF 2,3,5-TRIAMINOPYRIDINE AND USE OF THE SAME FOR DYEING KERATIN FIBERS

(75) Inventors: Aziz Fadli, Chelles (FR); Laurent Vidal, Paris (FR)

(73) Assignee: L'Oreal S.A., Paris (FR)

( * ) Notice: Subject to any disclaimer, the term of this patent is extended or adjusted under 35 U.S.C. 154(b) by 146 days.

(21) Appl. No.: 10/798,454

(22) Filed: Mar. 12, 2004

(65) Prior Publication Data

US 2005/0081313 A1   Apr. 21, 2005

Related U.S. Application Data

(60) Provisional application No. 60/467,124, filed on May 2, 2003.

(30) Foreign Application Priority Data

Mar. 13, 2003   (FR) .................................. 03 03114

(51) Int. Cl.
  *A61K 7/13*   (2006.01)
(52) U.S. Cl. ..................... 8/405; 8/406; 8/410; 8/411; 8/421; 548/579; 546/184; 546/250; 544/106
(58) Field of Classification Search ............ 8/405, 8/406, 410, 411, 421; 548/579; 546/184, 546/249, 250; 544/106
  See application file for complete search history.

(56) References Cited

U.S. PATENT DOCUMENTS

| 3,862,157 A | 1/1975 | Wiskott ................. 260/293.69 |
| 4,661,115 A | 4/1987 | Orth et al. ...................... 8/409 |
| 4,734,418 A * | 3/1988 | Yokoyama et al. ..... 514/252.16 |
| 2004/0060125 A1 | 4/2004 | Audouset ........................ 8/405 |

FOREIGN PATENT DOCUMENTS

| DE | 1 949 750 | 4/1971 |
| EP | 0 441 263 A1 | 8/1991 |
| FR | 1 397 551 | 4/1953 |
| GB | 2 104 922 A | 3/1983 |
| JP | 49-50144 | 5/1974 |
| JP | 58-34857 | 3/1983 |
| JP | 61-218512 | 9/1986 |
| JP | 4-120013 | 4/1992 |
| WO | WO 01/78668 A1 | 10/2001 |

OTHER PUBLICATIONS

STIC Search Report (p. 39, Alexandria Journal of Pharmaceutical Sciences (1996) 10(2), 113-116).*
STIC Search Report (p. 43, Journal of the Chemical Society, Perkin (1972-1999) (1991), (4), 509-13 ).*
Michael R. Crampton et al., "Kinetic and equilibrium studies of σ-adduct formation and nucleophilic substitution in the reactions of 2-phenoxy-3,5-dinitropyridine and 2-ethoxy-3,5-dinitropyridine with aliphatic amines in dipolar aprotic solvents," Organic and Biomolecular Chemistry, vol. 1, No. 6, 2003, pp. 1004-1011.
Fatma El Zahraa M. Elhegazy, "Kinetics of Nucleophilic Aromatic Substitution of Morpholine with Halo Nitro Compounds, Comparison of Activation Between Aza and Nitro Groups," Alexandria Journal of Pharmaceutical Sciences, vol. 10, No. 2, Jun. 1996, pp. 113-116.
Chemical Abstracts Service, Columbus, Ohio, US; Database accession No. 59:62817, XP002265349.
English language Derwent Abstract for JP 49-50144.
First Office Action issued in Japanese Patent Application No. 2004-071608 (English translation).

* cited by examiner

*Primary Examiner*—Eisa Elhilo
(74) *Attorney, Agent, or Firm*—Finnegan, Henderson, Farabow, Garrett & Dunner, LLP

(57) ABSTRACT

The present invention relates to a dye composition comprising at least one oxidation base and at least one coupler of the 2,3,5-triaminopyridine type. This composition may be useful for dyeing keratin fibers, such as the hair. Also disclosed are a process for dyeing keratin fibers and a multi-compartment dyeing kit using the claimed dye composition.

Such a composition can make it possible to obtain strong, uniform dyeing results between the end and the root, which are resistant to external agents, while at the same time being capable of giving varied shades, for example, in fundamental shades such as chestnut, grey or black shades.

29 Claims, No Drawings

COUPLERS OF 2,3,5-TRIAMINOPYRIDINE AND USE OF THE SAME FOR DYEING KERATIN FIBERS

This application claims benefit of U.S. Provisional Application No. 60/467,124, filed May 2, 2003, the entire disclosure and subject matter of which is hereby incorporated herein by reference.

Disclosed herein is a dye composition that is useful for dyeing keratin fibers, comprising at least one oxidation base and at least one coupler of the 2,3,5-triaminopyridine type, wherein the amino radical in position 2 forms a heterocyclic radical. Also disclosed herein is a process for dyeing keratin fibers using this composition. The disclosure also relates to novel compounds of the 2,3,5-triaminopyridine type that can be useful as couplers.

It is known practice to dye keratin fibers, and for example, human hair, with dye compositions containing oxidation dye precursors, which are generally known as oxidation bases, such as ortho- or para-phenylenediamines, ortho- or para-aminophenols, and heterocyclic compounds. These oxidation bases can be colorless or weakly colored compounds which, when combined with oxidizing products, can give rise to colored compounds by a process of oxidative condensation.

It is also known that the shades obtained with these oxidation bases can be varied by combining them with couplers or coloration modifiers, these agents being chosen, for example, from aromatic meta-diamines, meta-aminophenols, meta-diphenols and certain heterocyclic compounds such as indole compounds.

The variety of molecules used as oxidation bases and couplers allows a wide range of colors to be obtained.

It is desirable for the "permanent" coloration obtained by means of these oxidation dyes to satisfy a certain number of requirements. For example, such a coloration typically has at least one of the following properties: no toxicological drawbacks, allows shades to be obtained in the desired strength, and shows good fastness with respect to external agents such as light, bad weather, washing, permanent-waving, perspiration, and rubbing.

Other properties that may be possessed by such dyes include: allowing white hair to be covered and being as unselective as possible, i.e., producing the smallest possible differences in coloration along the same keratin fiber, which is generally differently sensitized (i.e., damaged) between its end and its root.

Document FR 1 397 551 describes dye compositions containing oxidation dye precursors of the trisubstituted pyridine derivative type, each of the substituents possibly being a hydroxyl, alkoxy, amino or $NR_1R_2$ radical with $R_1$ and $R_2$ representing a H, alkyl or aryl. The coloration is obtained either by oxidation in air or with an oxidizing medium containing aqueous hydrogen peroxide solution at basic pH. On account of the high oxidizability of these pyridine precursors, the dyeing results obtained on the hair have a tendency to change over time by changing color, which turns out to be particularly unattractive.

However, few, if any, of these compositions make it possible to obtain strong colorations in varied shades that are uniform between the root and the end of the hairs, that show little selectivity and particularly good resistance, and that have good chromaticity.

Thus, the present inventors propose dye compositions for dyeing keratin fibers, which do not have some or all of the drawbacks of the compositions of the prior art. For example, the dye compositions may make it possible to obtain strong, uniform dyeing results between the end and the root and may be resistant to external agents, while at the same time being capable of giving varied shades, for example, in fundamental shades such as chestnut, grey or black shades.

Thus, disclosed herein is a dye composition comprising, in a medium that is suitable for dyeing:
- at least one oxidation base, and
- at least one 2,3,5-triaminopyridine coupler of formula (I), or a corresponding addition salt thereof:

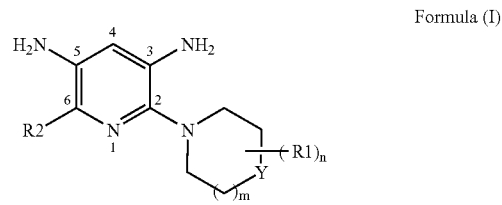

Formula (I)

wherein:
$R_1$ is chosen from:
- a halogen atom, such as fluorine, chlorine or bromine;
- a $C_1$–$C_4$ alkyl radical optionally substituted with at least one radical chosen from hydroxyl, carboxyl, ($C_1$–$C_4$) alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
- a carboxyl radical;
- a ($C_1$–$C_4$)alkoxycarbonyl radical;
- a carboxamido radical; ($NH_2CO$—)
- a ($C_1$–$C_4$)alkylcarboxamido radical; (alkyl-NHCO— or (alkyl)$_2$NCO—)
- a sulphinic radical; ($HSO_2$—)
- a $C_1$–$C_4$ alkylsulphonyl radical; (—$SO_2$-alkyl)
- a $C_1$–$C_4$ alkylsulphonamido radical; (alkylSO$_2$NH—)
- a hydroxyl radical;
- a $C_1$–$C_4$ alkoxy radical;
- a $C_2$–$C_4$ hydroxyalkoxy radical;
- a radical chosen from amino, monoaminoalkoxy and diaminoalkoxy radicals;
- a $C_1$–$C_4$ thioether radical;
- a $C_1$–$C_4$ alkylsulphoxy radical; (alkylSO—);
- a sulphonic radical; (—$SO_3H$); and
- a radical $NR_5R_6$;

$R_3$, $R_4$, $R_5$ and $R_6$, which may be identical or different, are chosen from a hydrogen atom; a $C_1$–$C_4$ alkylsulphonyl radical; a ($C_1$–$C_4$) alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and (di)($C_1$–$C_4$)alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, (di)($C_1$–$C_4$)alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals, n is an integer ranging from 0 to 7, m is 0, 1 or 2, Y is chosen from an oxygen atom, a radical $C(R_8)_2$ and a radical $NR_7$ in which $R_7$ has the same meaning as $R_3$, and $R_8$, which may be identical or different, is chosen from hydrogen or has the same meaning as $R_1$.

Also disclosed herein is a process for dyeing keratin fibers, and also a device for dyeing using the disclosed composition.

Finally, disclosed herein are the compounds of formula (I) and also the intermediate nitro compounds in the synthesis of the compounds of formula (I).

In the context of the present disclosure, the term "alkyl" means linear or branched radicals, for example methyl, ethyl, n-propyl, isopropyl, butyl, etc. An alkoxy radical can be an alkyl-O radical, the alkyl radical having the definition given above.

In the above formula, $R_1$, for example, is chosen from a $C_1$–$C_4$ alkoxy radical optionally substituted with at least one radical chosen from hydroxyl, $C_1$–$C_2$ alkoxy, amino or (di)alkylamino radicals; a hydroxyl radical; an amino radical; a (di)alkylamino radical; and a $C_1$–$C_2$ alkyl radical optionally substituted with a hydroxyl or an amino.

According to another embodiment, $R_2$ is chosen from a hydrogen atom and an alkoxy radical.

In the above formula (I), n, for example, is 0 or 1.

$R_3$, $R_4$, $R_5$, $R_6$ and $R_7$, which may be identical or different, may be chosen from a hydrogen atom, a carboxamido radical and a $C_1$–$C_4$ alkyl radical optionally substituted with at least one radical chosen from hydroxyl, $C_1$–$C_4$ alkoxy, carboxamido, amino, (di)($C_1$–$C_4$)alkylamino and $C_2$–$C_4$ (poly)hydroxyalkylamino radicals.

For example, $R_3$, $R_4$, $R_5$, $R_6$ and $R_7$, which may be identical or different, are chosen from a hydrogen atom and from methyl, ethyl, 2-carboxyethyl, 2-hydroxyethyl, 3-hydroxypropyl, 2,3-dihydroxypropyl, 2-hydroxy-3-aminopropyl and 3-hydroxy-2-aminopropyl radicals. According to a further embodiment, $R_3$, $R_4$, $R_5$, $R_6$ and $R_7$, which may be identical or different, are chosen from a hydrogen atom, a methyl radical, a 2-hydroxyethyl radical and a 2,3-dihydroxypropyl radical.

For example, at least one of the radicals $R_8$ is hydrogen.

In formula (I), the nitrogen in position 2 of the ring, together with Y and m, may form a heterocyclic radical chosen from pyrrolidines, piperidines, homopiperidines, piperazines, homopiperazines and diazepanes (or 1,4-diazacycloheptane).

According to one embodiment, the heterocycle is chosen from pyrrolidine, 2,5-dimethylpyrrolidine, 2-methylpyrrolidine, proline, 3-hydroxyproline, 4-hydroxyproline, 2,4-dicarboxypyrrolidine, 2-hydroxymethylpyrrolidine, 3-hydroxy-2-hydroxymethyl-pyrrolidine, 2,5-di(hydroxymethyl)pyrrolidine, 2-carboxamidopyrrolidine, 3-hydroxy-2-carboxamidopyrrolidine, 2-(dimethylcarboxamido)pyrrolidine, 2-(dimethylcarboxamido)-3-hydroxypyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylamino-pyrrolidine, 4-amino-3-hydroxypyrrolidine, 4-methylamino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-(dimethylcarboxamido) piperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, piperazine, 4-methylpiperazine, diazepane, N-methyl-homopiperazine and N-β-hydroxyethylhomopiperazine, and the addition salts thereof.

For example, the heterocycle may be chosen from pyrrolidine, 2-methylpyrrolidine, 3-hydroxypyrrolidine, 3-aminopyrrolidine, 3-(methylsulphonylamino)pyrrolidine, proline, 3-hydroxyproline, piperidine, hydroxypiperidine, homopiperidine, 4-methylpiperazine, diazepane, N-methylhomopiperazine and N-β-hydroxyethylhomopiperazine, and the addition salts thereof.

According to yet another embodiment, the heterocycle is chosen from pyrrolidine, 3-hydroxypyrrolidine, 3-aminopyrrolidine, 3-(methylsulphonylamino)pyrrolidine, proline and 3-hydroxyproline.

According to a further embodiment, in formula (I), $R_1$ is chosen from alkyl, amino, hydroxyalkyl and hydroxyl radicals, $R_2$ is hydrogen, m is 0 or 1, and n ranges from 0 to 2.

The compounds of formula (I) that may be useful herein are, for example, the following compounds:

N-(3,5-diaminopyrid-2-yl)pyrrolidine;
N-(3,5-diaminopyrid-2-yl)-2-methylpyrrolidine;
N-(3,5-diaminopyrid-2-yl)-2,5-dimethylpyrrolidine;
N-(3,5-diaminopyrid-2-yl)-2-hydroxymethylpyrrolidine;
N-(3,5-diaminopyrid-2-yl)proline;
N-(3,5-diaminopyrid-2-yl)-3-hydroxypyrrolidine;
N-(3,5-diaminopyrid-2-yl)-2-hydroxymethyl-3-hydroxypyrrolidine;
N-(3,5-diaminopyrid-2-yl)-2-carboxamidopyrrolidine;
N-(3,5-diaminopyrid-2-yl)-2-dimethylcarboxamidopyrrolidine;
N-(3,5-diaminopyrid-2-yl)-3,4-dihydroxypyrrolidine;
N-(3,5-diaminopyrid-2-yl)-3-aminopyrrolidine;
N-(3,5-diaminopyrid-2-yl)-3-dimethylaminopyrrolidine;
N-(3,5-diaminopyrid-2-yl)piperidine;
N-(3,5-diaminopyrid-2-yl)-2,5-dimethylpiperidine;
N-(3,5-diaminopyrid-2-yl)-2-hydroxymethylpiperidine;
N-(3,5-diaminopyrid-2-yl)-2-carboxypiperidine;
N-(3,5-diaminopyrid-2-yl)-3-hydroxypiperidine;
N-(3,5-diaminopyrid-2-yl)-2-carboxamidopiperidine;
N-(3,5-diaminopyrid-2-yl)-2-dimethylcarboxamidopiperidine;
N-(3,5-diaminopyrid-2-yl)-4-hydroxypiperidine;
N-(3,5-diaminopyrid-2-yl)homopiperidine;
N-(3,5-diaminopyrid-2-yl)-2-carboxyhomopiperidine;
N-(3,5-diaminopyrid-2-yl)-4-methylpiperazine;
N-(3,5-diaminopyrid-2-yl)homopiperazine;
N-(3,5-diaminopyrid-2-yl)-N'-methylhomopiperazine;
N-(3,5-diaminopyrid-2-yl)-6-methoxypyrrolidine;
N-(3,5-diaminopyrid-2-yl)-6-methoxy-2,5-dimethylpyrrolidine;
N-(3,5-diaminopyrid-2-yl)-6-methoxy-2-hydroxymethylpyrrolidine;
N-(3,5-diaminopyrid-2-yl)-6-methoxyproline;
N-(3,5-diaminopyrid-2-yl)-6-methoxy-3-hydroxypyrrolidine;
N-(3,5-diaminopyrid-2-yl)-6-methoxy-2-hydroxymethyl-3-hydroxypyrrolidine;
N-(3,5-diaminopyrid-2-yl)-6-methoxy-2-carboxamidopyrrolidine;
N-(3,5-diaminopyrid-2-yl)-6-methoxy-2-dimethylcarboxamidopyrrolidine;
N-(3,5-diaminopyrid-2-yl)-6-methoxy-3,4-dihydroxypyrrolidine;
N-(3,5-diaminopyrid-2-yl)-6-methoxy-3-aminopyrrolidine;
N-(3,5-diaminopyrid-2-yl)-6-methoxy-3-dimethylaminopyrrolidine;
N-(3,5-diaminopyrid-2-yl)-6-methoxypiperidine;
N-(3,5-diaminopyrid-2-yl)-6-methoxy-2,5-dimethylpiperidine;

N-(3,5-diaminopyrid-2-yl)-6-methoxy-2-hydroxymethylpiperidine;
N-(3,5-diaminopyrid-2-yl)-6-methoxy-2-carboxypiperidine;
N-(3,5-diaminopyrid-2-yl)-6-methoxy-3-hydroxypiperidine;
N-(3,5-diaminopyrid-2-yl)-6-methoxy-2-carboxamidopiperidine;
N-(3,5-diaminopyrid-2-yl)-6-methoxy-2-dimethylcarboxamidopiperidine;
N-(3,5-diaminopyrid-2-yl)-6-methoxy-4-hydroxypiperidine;
N-(3,5-diaminopyrid-2-yl)-6-methoxyhomopiperidine;
N-(3,5-diaminopyrid-2-yl)-6-methoxy-2-carboxyhomopiperidine;
N-(3,5-diaminopyrid-2-yl)-6-methoxyhomopiperazine;
N-(3,5-diaminopyrid-2-yl)-6-methoxy-N'-methylhomopiperazine; and the addition salts thereof.

In another embodiment, the compounds of formula (I) may be chosen from:
N-(3,5-diaminopyrid-2-yl)pyrrolidine;
N-(3,5-diaminopyrid-2-yl)-2-methylpyrrolidine;
N-(3,5-diaminopyrid-2-yl)-2,5-dimethylpyrrolidine;
N-(3,5-diaminopyrid-2-yl)-2-hydroxymethylpyrrolidine;
N-(3,5-diaminopyrid-2-yl)proline;
N-(3,5-diaminopyrid-2-yl)-3-hydroxypyrrolidine;
N-(3,5-diaminopyrid-2-yl)-2-carboxamidopyrrolidine;
N-(3,5-diaminopyrid-2-yl)-2-dimethylcarboxamidopyrrolidine;
N-(3,5-diaminopyrid-2-yl)-3,4-dihydroxypyrrolidine;
N-(3,5-diaminopyrid-2-yl)-3-aminopyrrolidine;
N-(3,5-diaminopyrid-2-yl)-3-dimethylaminopyrrolidine;
N-(3,5-diaminopyrid-2-yl)piperidine;
N-(3,5-diaminopyrid-2-yl)-4-methylpiperazine;
and the addition salts thereof.

The oxidation dye composition disclosed herein comprises at least one oxidation base conventionally used in oxidation dyeing. By way of example, the at least one oxidation base may be chosen from para-phenylenediamines other than those described above, bis(phenyl)alkylenediamines, para-aminophenols, bis-para-aminophenols, ortho-aminophenols and heterocyclic bases, and the addition salts thereof.

Among the para-phenylenediamines that may be mentioned, for example, can be para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the acid addition salts thereof.

For example, the the para-phenylenediamines may be chosen from para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine and 2-β-acetylaminoethyloxy-para-phenylenediamine, and the acid addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

Among the ortho-aminophenols that may be mentioned, for example, are 2-aminophenol, 2-amino-5-methylphenol, 2-amino-6-methylphenol and 5-acetamido-2-aminophenol, and the acid addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, and 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof Other pyridine oxidation bases that may be useful are the 3-aminopyrazolo[1,5-a]pyridine oxidation bases or addition salts thereof described, for example, in patent application FR 2 801 308. Examples that may be mentioned comprise pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof with an acid or with a base.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The at least one oxidation base present in the dye composition disclosed herein may be present in an amount ranging from 0.001% to 10% by weight approximately, and for example, from 0.005% to 6% by weight approximately, relative to the total weight of the dye composition.

The composition disclosed herein may also comprise at least one conventional coupler in the field of dyes other than the couplers of formula (I). Among these additional couplers, those that may be mentioned, for example, are meta-phenylenediamines, meta-aminophenols, meta-diphenols, naphthalene-based couplers and heterocyclic couplers and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid addition salts thereof.

In the composition disclosed herein, the coupler(s), i.e., the at least one 2,3,5-triaminopyridine coupler and any additional coupler(s), may be present in an amount ranging from 0.001% to 10% by weight approximately, and for example, from 0.005% to 6% by weight approximately, relative to the total weight of the dye composition.

In general, the addition salts of the oxidation bases and of the couplers that may be used in the context of the present disclosure are chosen, for example, from the acid addition salts, such as the hydrochlorides, hydrobromides, sulphates, citrates, succinates, tartrates, lactates, tosylates, benzenesulphonates, phosphates and acetates, and the base addition salts, such as sodium hydroxide, potassium hydroxide, aqueous ammonia, amines or alkanolamines.

The dye composition in accordance with at least one embodiment herein may also comprise at least one direct dye that may be chosen from, for example, nitrobenzene dyes, azo direct dyes and methine direct dyes. These direct dyes may be of nonionic, anionic or cationic nature.

The dye composition disclosed herein may be useful for dyeing keratin fibers, such as human keratin fibers. The medium may be a cosmetic medium that is suitable for dyeing these fibers.

This medium suitable for dyeing, also known as a dye support, generally comprises water or a mixture of water and at least one organic solvent to dissolve the compounds that would not be sufficiently soluble in the water. Examples of organic solvents that may be mentioned include $C_1$–$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are, for example, present in proportions ranging from 1% to 40% by weight approximately, such as ranging from 5% to 30% by weight approximately, relative to the total weight of the dye composition.

The dye composition disclosed herein may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and for example, anionic, cationic, nonionic and amphoteric polymeric associative thickeners, antioxidants, penetrating agents, sequestering agents, fragrances, buffers, dispersants, conditioners, for instance volatile or non-volatile, modified or unmodified silicones, film-forming agents, ceramides, preserving agents and opacifiers.

The above adjuvants may be present in an amount for each ranging from 0.01% to 20% by weight approximately, relative to the total weight of the dye composition.

Needless to say, a person skilled in the art should take care to select this or these additional optional compound(s) such that the advantageous properties intrinsically associated with the oxidation dye composition in accordance with at least one embodiment may not, or may not substantially, be adversely affected by the envisaged addition(s).

The pH of the dye composition disclosed herein ranges from 3 to 12 approximately and for example, ranges from 5 to 11 approximately. It may be adjusted to the desired value by means of acidifying or basifying agents usually used for dyeing keratin fibers, or alternatively using standard buffer systems.

Among the acidifying agents that may be mentioned, for example, are mineral or organic acids, for instance hydrochloric acid, orthophosphoric acid, sulphuric acid, carboxylic acids, for instance acetic acid, tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (III) below:

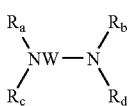
(III)

in which W is a propylene residue optionally substituted with a hydroxyl group or a $C_1$–$C_4$ alkyl radical; $R_a$, $R_b$, $R_c$ and $R_d$, which may be identical or different, are chosen from a hydrogen atom, and from $C_1$–$C_4$ alkyl and $C_1$–$C_4$ hydroxyalkyl radicals.

The dye composition disclosed herein may be in various forms, such as in the form of liquids, creams or gels, or in any other form that is suitable for dyeing keratin fibers, and for example, human hair.

The process disclosed herein is a process in which the dye composition as defined above is applied to the fibers, in the presence of an oxidizing agent, for a time that is sufficient to develop the desired coloration. The color may be revealed at acidic, neutral or alkaline pH and the oxidizing agent may be added to the dye composition just at the time of use, or it may be introduced using an oxidizing composition containing it, applied simultaneously with or sequentially to the dye composition.

According to at least one embodiment, the dye composition disclosed herein is mixed, for example, at the time of use, with a composition comprising, in a medium that is suitable for dyeing, at least one oxidizing agent, this oxidizing agent being present in an amount that is sufficient to develop a coloration. The mixture obtained is then applied to the keratin fibers. After a leave-in time ranging from 3 to 50 minutes approximately and for example, ranging from 5 to 30 minutes approximately, the keratin fibers are rinsed, washed with shampoo, optionally rinsed again, and then dried.

The oxidizing agents conventionally used for the oxidation dyeing of keratin fibers may be, for example, hydrogen peroxide, urea peroxide, alkali metal bromates, persalts such as perborates and persulphates, peracids, and oxidase enzymes, among which mention may be made of peroxidases, 2-electron oxidoreductases such as uricases, and 4-electron oxygenases, for instance laccases. In one embodiment, the oxidizing agent used is hydrogen peroxide.

The oxidizing composition may also contain various adjuvants conventionally used in hair dye compositions and as defined above.

The pH of the oxidizing composition containing the oxidizing agent is such that, after mixing with the dye composition, the pH of the resulting composition applied to the keratin fibers for example, ranges from 3 to 12 approximately and for example, ranges from 5 to 11 approximately. Further, the pH may range from 6 to 8 approximately. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels, or in any other form that is suitable for dyeing keratin fibers, and for example, human hair.

The composition disclosed herein may be in the form of a kit. Such a kit comprises a dye composition as defined above, and an oxidizing composition.

A further embodiment is a multi-compartment kit, in which a first compartment comprises the dye composition defined above and a second compartment comprises an oxidizing agent. This kit may be equipped with a means for applying the desired mixture to the hair, such as the devices described in patent FR 2 586 913 in the name of the Applicant.

Using this kit, it may be possible to dye keratin fibers using a process that involves mixing a dye composition as disclosed herein with an oxidizing agent, and applying the mixture obtained to the keratin fibers for a time that is sufficient to develop the desired coloration.

Further, additionally disclosed herein are the 2,3,5-triaminopyridine compounds of formula (I), and also the corresponding addition salts thereof as defined above.

These compounds may be synthesized according to the following synthetic scheme:

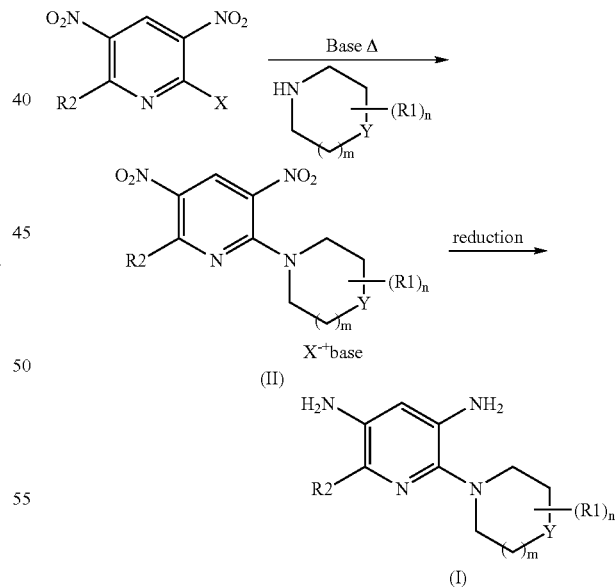

X is chosen from a halogen atom such as a chlorine or bromine, or a $C_1$–$C_2$ alkoxy radical, and $R_2$, $R_1$, n and m are as defined above.

The compounds of formula (II) may be obtained by dissolving, with stirring, a 2-halo-3,5-dinitropyridine or 2-alkoxy-3,5-dinitropyridine such as 2-chloro-3,5-dinitropyridine or 2-methoxy-3,4-dinitropyridine in a protic or aprotic solvent with a boiling point of between 60° C. and 180° C., for instance dioxane, DMF, THF, a lower alcohol or water, and in the presence of an organic or mineral base that can form a salt with the ion released. The cyclic amine is then introduced dropwise. The temperature of the reaction medium generally ranges from 25° C. to 100° C. After disappearance of the reagents, the reaction medium is cooled to room temperature and poured into a mixture of ice and water. The precipitate thus formed is filtered off by suction of a sinter funnel, washed with water and then dried under vacuum to constant weight.

The compounds of formula (I) may then be obtained by reducing the nitro precursors of formula (II) either by catalytic hydrogenation, or by hydrogen transfer, or with a metal such as zinc, tin or iron, or with a hydride such as sodium borohydride or lithium aluminium hydride. For example, the reaction used can be heterogeneous catalytic hydrogenation or phase-transfer with cyclohexene. The solvent may be a protic or aprotic solvent and for example, an alcohol with a boiling point ranging from 66° C. to 160° C. The catalyst may be conventionally palladium-on-charcoal. The hydrogenation reaction may be generally performed at a temperature ranging from 25° C. to 80° C. under a hydrogen pressure ranging from 1 bar to 40 bar and for example, ranging from 1 bar to 8 bar.

Disclosed herein are also the nitro compounds of formula (II)

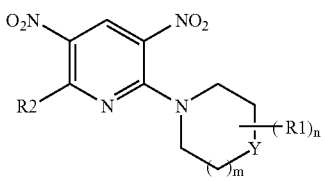

in which $R_2$, $R_1$, Y, n and m are as defined above.

For example, in the above formula, when $R_2$ is chosen from hydrogen, then the heterocycle is not chosen from a pyrrolidine (n=0, m=0, Y=CH), a piperidine (n=0, m=1, Y=CH) and a piperazine (n=0, m=1, Y=NH).

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES OF SYNTHESIS

Example 1

N-(3,5-diaminopyrid-2-yl)pyrrolidine dihydrochloride monohydrate

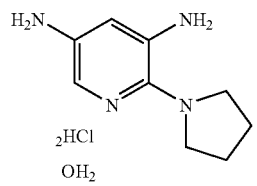

Protocol A:

Synthesis of 3.5-dinitro-2-pyrrolidin-1-ylpyridine 2.2 g (0.03 mol) of pyrrolidine were added over 10 minutes to a solution containing 3 g (0.015 mol) of 2-chloro-3,5-dinitropyridine in 30 ml of dioxane, at 40° C. The reaction medium was maintained at 60° C. until the reagents disappeared. The reaction medium was then poured into a water/ice mixture with vigorous stirring and the precipitate was filtered off by suction, washed with water and then dried to constant weight to give 3.2 g of 3,5-dinitro-2-pyrrolidin-1-ylpyridine.

The mass spectrometry and NMR analyses were in compliance.

Protocol B:

Synthesis of N-(3,5-diaminopyrid-2-yl)pyrrolidine•x HCl•y H₂O•z ROH 4 g (0.0168 mol) of 3,5-dinitro-2-pyrrolidin-1-ylpyridine, obtained according to Protocol A from 2-chloro-3,5-dinitropyridine and pyrrolidine, was reduced in an autoclave in 100 ml of ethanol in the presence of 10% palladium-on-charcoal under a pressure of 8 bar at room temperature. After disappearance of the reagents, the catalyst was removed by filtration, the filtrate was acidified with hydrochloric acid and the reduced derivative was isolated in the form of the dihydrochloride monohydrate.

After drying, 3.7 g of solid was obtained.

Elemental analysis of the dihydrochloride monohydrate

| Theory | C: 40.16 | H: 6.74 | N: 20.81 | Cl: 26.34 |
| Found | C: 40.43 | H: 6.30 | N: 20.34 | Cl: 26.82 |

Example 2

Synthesis of N-(3,5-diaminopyrid-2-yl)-3-hydroxypyrrolidine dihydrochloride

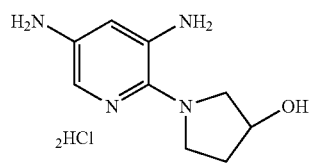

2 g (0.01 mol) of 3,5-dinitro-2-(3-hydroxypyrrolidin-1-yl)pyridine obtained according to Protocol A from 2-chloro- 3,5-dinitropyridine and 3-hydroxypyrrolidine, were reduced according to Protocol B, to give 1.1 g of N-(3,5-diaminopyrid-2-yl)-3-hydroxypyrrolidine dihydrochloride.

After drying, 0.9 g of solid was obtained.

The NMR and mass spectrometry analyses were in accordance with the expected structure.

Example 3

Synthesis of N-(3,5-diaminopyrid-2-yl)-2-methylpyrrolidine•1.8 HCl•1 MeOH

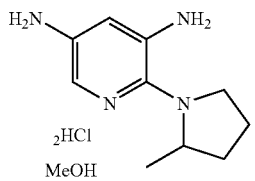

1.5 g (5.94 mmol) of (2-methylpyrrolidin-1-yl)-3,5-dinitropyridine, obtained according to Protocol A from 2-chloro-3,5-dinitropyridine and 2-methylpyrrolidine, were reduced by hydrogen transfer in 50 ml of ethanol in the presence of palladium-on-charcoal and 5 ml of cyclohexene. After filtering off the catalyst, the hydrochloride salt was isolated by using, during the treatment, a methanolic hydrogen chloride solution. N-(3,5-Diaminopyrid-2-yl)(2-methyl)pyrrolidine•1.8 HCl•1 MeOH was obtained.

After drying to constant weight, 890 mg of solid were obtained.

Theoretical elemental analysis with 1.8 mol of hydrochloric acid and one mole of methanol:

| Theory | C: 45.56 | H: 7.52 | N: 19.33 | Cl: 22.07 |
| --- | --- | --- | --- | --- |
| Found | C: 45.99 | H: 7.25 | N: 19.00 | Cl: 22.92 |

Example 4

Synthesis of N-(3,5-diaminopyrid-2-yl)-2,5-dimethylpyrrolidine dihydrochloride:

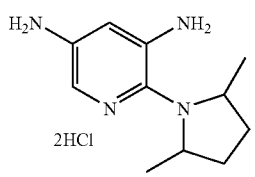

1.5 g (5.63 mmol) of (2,5-dimethylpyrrolidin-1-yl)-3,5-dinitropyridine, obtained according to Protocol A from 2-chloro-3,5-dinitropyridine and 2,5-dimethylpyrrolidine, were reduced by hydrogen transfer in 50 ml of ethanol in the presence of palladium-on-charcoal and 5 ml of cyclohexene. 900 mg of N-(3,5-diaminopyrid-2-yl)-2,5-dimethylpyrrolidine dihydrochloride were obtained.

The NMR and mass spectrometry analyses were in accordance with the expected structure.

Example 5

Synthesis of N-(3,5-diaminopyrid-2-yl)piperidine•1.9 HCl monohydrate

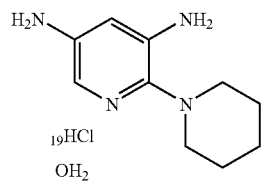

2 g of (1-piperidyl)-3,5-dinitropyridine, obtained according to Protocol A from 2-chloro-3,5-dinitropyridine and piperidine, were reduced by hydrogen transfer in 50 ml of ethanol in the presence of palladium-on-charcoal and 5 ml of cyclohexene. 930 mg of N-(3,5-diaminopyrid-2-yl)piperidine dihydrochloride were thus obtained.

Theoretical elemental analysis of the monohydrate with 1.9 HCl:

| Theory | C: 42.96 | H: 7.12 | N: 20.05 | Cl: 24.14 |
| --- | --- | --- | --- | --- |
| Found | C: 43.74 | H: 7.12 | N: 19.57 | Cl: 23.99 |

Example 6

Synthesis of 2-(4-methylpiperazin-1-yl)pyridine-3,5-diamine dihydrochloride

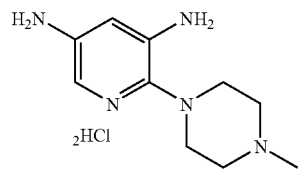

2 g of 1-(3,5-dinitropyrid-2-yl)-4-methylpiperazine, obtained according to Protocol A from 2-chloro-3,5-dinitropyridine and 4-methylpiperazine, were reduced by hydrogen transfer in 50 ml of ethanol in the presence of palladium-on-charcoal and 5 ml of cyclohexene. 1.63 g of 2-(4-methylpiperazin-1-yl)pyridine-3,5-diamine were obtained.

The NMR and mass spectrometry analyses were in accordance with the expected structure:

Example 7

Synthesis of (4-ethylpiperazin-1-yl)pyridine-3,5-diamine trihydrochloride

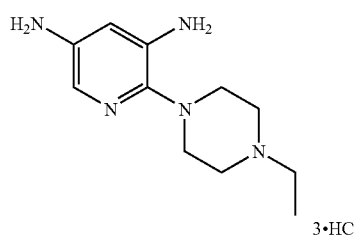

A) Synthesis of (4-ethylpiperazin-1-yl)-3,5-dinitropyridine 3 g (14.7 mmol) of 2-chloro-3,5-dinitropyridine, 20 ml of THF and 30 mmol of 4-ethylpiperazine were placed in a round-bottomed flask. The mixture was maintained at 60° C. for two hours with stirring and was then poured into a mixture of ice-water with stirring. The precipitate formed was filtered off by suction and dried under vacuum to constant weight. 5 g of yellow powder were obtained.

The NMR and mass spectrometry analyses were in accordance with the expected structure.

B) Synthesis of (4-ethylpiperazin-1-yl)pyridine-3,5-diamine trihydrochloride 0.8 g (2.8 mmol) of (4-ethylpiperazin-1-yl)-3,5-dinitropyridine, synthesized according to procedure (A) above, 10 ml of ethanol, 2 ml of cyclohexene and 0.5 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 0.41 g of powder was obtained.

The NMR and mass spectrometry analyses were in accordance with the expected structure.

Elemental Analysis:

C, 36.87%; H, 7.05%; N, 19.73%; Cl, 29.41%; O, 5.69%.

Example 8

Synthesis of 2-(3,5-dimethylpiperid-1-yl)pyridine-3,5-diamine dihydrochloride

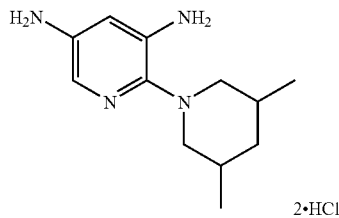

A) Synthesis of 2-(3,5-dimethylpiperid-1-yl)-3,5-dinitropyridine 2 g (9.82 mmol) of 2-chloro-3,5-dinitropyridine, 10 ml of THF and 20 mmol of 3,5-dimethylpiperidine were placed in a round-bottomed flask. he mixture was maintained at 60° C. for 15 hours with stirring and was then poured into a mixture of ice-water with stirring. The precipitate formed was filtered off by suction and dried under vacuum to constant weight. 2.55 g of yellow powder were obtained.

The NMR and mass spectrometry analyses were in accordance with the expected structure.

B) Synthesis of 2-(3,5-dimethylpiperid-1-yl)pyridine-3,5-diamine dihydrochloride 1.27 g (7 mmol) of 2-(3,5-dimethylpiperid-1-yl)-3,5-dinitropyridine, synthesized according to procedure (A) above, 20 ml of ethanol, 5 ml of cyclohexene and 1 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 1.32 g of powder were obtained.

The NMR and mass spectrometry analyses were in accordance with the expected structure.

Elemental Analysis:

C, 48.71%; H, 7.92%; N, 18.96%; Cl, 23.08%; O, 3.03%.

Example 9

Synthesis of 2-(1-(3,5-diaminopyrid-2-yl)piperid-2-yl)ethanol dihydrochloride

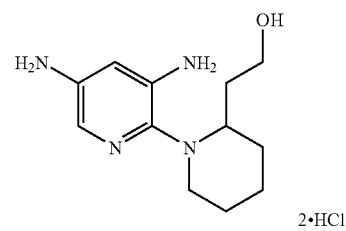

A) Synthesis of 2-(1-(3,5-dinitropyrid-2-yl)piperid-2-yl)ethanol 3 g (14.7 mmol) of 2-chloro-3,5-dinitropyridine, 1.0 ml of THF and 30 mmol of 2-piperidinethanol were placed in a round-bottomed flask. The mixture was maintained at 60° C. for 15 hours with stirring and was then poured into an ice-water mixture with stirring. The precipitate formed was filtered off by suction and dried under vacuum to constant weight. 3.71 g of yellow powder were obtained.

The NMR and mass spectrometry analyses were in accordance with the expected structure.

B) Synthesis of 2-(1-(3,5-diaminopyrid-2-yl)piperid-2-yl)ethanol dihydrochloride 1.95 g (6.6 mmol) of 2-(1-(3,5-dinitropyrid-2-yl)piperid-2-yl)ethanol, synthesized according to procedure (A) above, 20 ml of ethanol, 5 ml of cyclohexene and 1.5 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropylether, the precipitate formed was filtered off by suction and dried under vacuum to constant weight. 1.55 g of powder were obtained.

The NMR and mass spectrometry analyses were in accordance with the expected structure.

Elemental Analysis:

C, 44.27%; H, 7.6%; N, 16.34%; Cl, 22.16%; O, 10.30%.

Example 10

Synthesis of 1-(3,5-diaminopyrid-2-yl)piperidine-4-carboxamide dihydrochloride

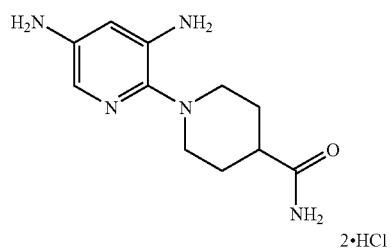

A) Synthesis of 1-(3,5-dinitropyrid-2-yl)piperidine-4-carboxamide 3 g (14.7 mmol) of 2-chloro-3,5-dinitropyridine, 10 ml of THF and 30 mmol of 4-piperidine carboxamide were placed in a round-bottomed flask. The mixture was maintained at 60° C. for 15 hours with stirring and was then poured into an ice-water mixture with stirring. The precipitate formed was filtered off by suction and dried under vacuum to constant weight. 0.522 g of yellow powder was obtained.

The NMR and mass spectrometry analyses were in accordance with the expected structure.

B) Synthesis of 1-(3,5-diaminopyrid-2-yl)piperidine-4-carboxamide dihydrochloride 1.93 g (6.5 mmol) of 1-(3,5-nitropyrid-2-yl)piperidine-4-carboxamide, synthesized according to procedure (A) above, 20 ml of ethanol, 5 ml of cyclohexene and 1.5 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 1.2 g of powder were obtained.

The NMR and mass spectrometry analyses were in accordance with the expected structure.

Elemental Analysis:
C, 40.94%; H, 6.97%; N, 21.23%; Cl, 21.47%; O, 10.77%.

Example 11

Synthesis of 2-(2-methylpiperidin-1-yl)pyridine-3,5-diamine dihydrochloride

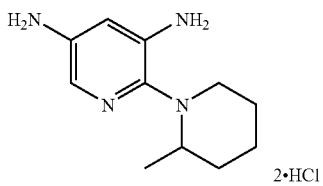

A) Synthesis of 2-(2-methylpiperidin-1-yl)-3,5-dinitropyridine 2.5 g (12.28 mmol) of 2-chloro-3,5-dinitropyridine, 10 ml of THF and 25 mmol of 2-methylpiperidine were placed in a round-bottomed flask. The mixture was maintained at 60° C. for 15 hours with stirring and was then poured into an ice-water mixture with stirring. The precipitate formed was filtered off by suction and dried under vacuum to constant weight. 3.09 g of yellow powder was obtained.

The NMR and mass spectrometry analyses were in accordance with the expected structure.

B) Synthesis of 2-(2-methylpiperidin-1-yl)pyridine-3,5-diamine dihydrochloride 1.72 g (6.5 mmol) of 2-(2-methylpiperidin-1-yl)-3,5-dinitropyridine, synthesized according to procedure (A) above, 20 ml of ethanol, 5 ml of cyclohexene and 1.5 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 1.24 g of powder were obtained.

The NMR and mass spectrometry analyses were in accordance with the expected structure.

Elemental Analysis:
C, 45.34%; H, 7.47%; N, 18.71%; Cl, 22.01%; O, 5.56%.

Example 12

Synthesis of 2-azepan-1-ylpyridine-3,5-diamine dihydrochloride

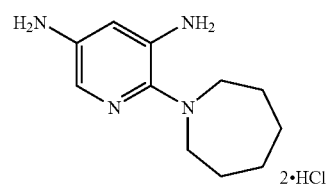

A) Synthesis of 2-azepan-1-yl-3,5-dinitropyridine 3 g (14.7 mmol) of 2-chloro-3,5-dinitropyridine, 10 ml of THF and 30 mmol of azepane were placed in a round-bottomed flask. The mixture was maintained at 60° C. for 15 hours with stirring and was then poured into an ice-water mixture with stirring. The precipitate formed was filtered off by suction and dried under vacuum to constant weight. 1.64 g of yellow powder were obtained.

The NMR and mass spectrometry analyses were in accordance with the expected structure.

B) Synthesis of 2-azepan-1-ylpyridine-3,5-diamine dihydrochloride 1.66 g (6.25 mmol) of 2-azepan-1-yl-3,5-dinitropyridine, synthesized according to procedure (A) above, 20 ml of ethanol, 5 ml of cyclohexene and 1.5 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 1.03 g of powder were obtained.

The NMR and mass spectrometry analyses were in accordance with the expected structure.

Elemental Analysis:
C, 40.46%; H, 6.88%; N, 18.47%; Cl, 23.37%; O, 9.74%.

Example 13

Synthesis of 2-morpholin-4-ylpyridine-3,5-diamine dihydrochloride

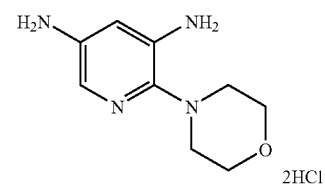

A) Synthesis of 2-morpholin-4-yl-3,5-dinitropyridine 5 g (24.5 mmol) of 2-chloro-3,5-dinitropyridine, 40 ml of THF and 50 mmol of morpholine were placed in a round-bottomed flask. The mixture was maintained at 60° C. for 15 hours with stirring and was then poured into an ice-water mixture with stirring. The precipitate formed was filtered off by suction and dried under vacuum to constant weight. 6.09 g of yellow powder were obtained.

The NMR and mass spectrometry analyses were in accordance with the expected structure.

B) Synthesis of 2-morpholin-4-ylpyridine-3,5-diamine dihydrochloride 3.5 g (13.76 mmol) of 2-morpholin-4-yl-3,5-dinitropyridine, synthesized according to procedure (A) above, 20 ml of ethanol, 5 ml of cyclohexene and 2 g of palladium-on-charcoal were placed in a fully equipped round-bottomed flask. The mixture was refluxed for two hours with stirring, the catalyst was then removed by filtration and the filtrate was then acidified with hydrochloric acid. After dilution with diisopropyl ether, the precipitate formed was filtered off by suction and dried under vacuum to constant weight. 0.98 g of powder was obtained.

The NMR and mass spectrometry analyses were in accordance with the expected structure.

EXAMPLES OF DYEING

Example A

Examples 1 to 24 of Dyeing in Alkaline Medium

| | Examples | | | | | | | |
|---|---|---|---|---|---|---|---|---|
| | 1 | 2 | 3 | 4 | 5 | 6 | 7 | 8 |
| N-(3,5-diamino-pyridin-2-yl)pyrrolidine | $4 \times 10^{-4}$ mol | | | | $4 \times 10^{-4}$ mol | | | |
| N-(3,5-diamino-pyridin-2-yl)-3-hydroxy-pyrrolidine | | $4 \times 10^{-4}$ mol | | | | $4 \times 10^{-4}$ mol | | |
| N-(3,5-diamino-pyridin-2-yl)-2-methylpyrrolidine | | | $4 \times 10^{-4}$ mol | | | | $4 \times 10^{-4}$ mol | |
| N-(3,5-diamino-pyridin-2-yl)piperidine | | | | $4 \times 10^{-4}$ mol | | | | $4 \times 10^{-4}$ mol |
| 7-methylamino-3-aminopyrazolo[1,5-a]pyrimidine dihydrochloride | $4 \times 10^{-4}$ mol | $4 \times 10^{-4}$ mol | $4 \times 10^{-4}$ mol | $4 \times 10^{-4}$ mol | | | | |
| 7-dimethylamino-3-aminopyrazolo[1,5-a]pyrimidine dihydrochloride | | | | | $4 \times 10^{-4}$ mol | $4 \times 10^{-4}$ mol | $4 \times 10^{-4}$ mol | $4 \times 10^{-4}$ mol |
| Dye support (1) | (*) | (*) | (*) | (*) | (*) | (*) | (*) | (*) |
| Demineralized water qs | 100 g | 100 g | 100 g | 100 g | 100 g | 100 g | 100 g | 100 g |

| | Examples | | | | | | | |
|---|---|---|---|---|---|---|---|---|
| | 9 | 10 | 11 | 12 | 13 | 14 | 15 | 16 |
| N-(3,5-diaminopyridin-2-yl)pyrrolidine | $4 \times 10^{-4}$ mol | | | | $4 \times 10^{-4}$ mol | | | |
| N-(3,5-diamino-pyridin-2-yl)-3-hydroxypyrrolidine | | $4 \times 10^{-4}$ mol | | | | $4 \times 10^{-4}$ mol | | |
| N-(3,5-diamino-pyridin-2-yl)-2-methylpyrrolidine | | | $4 \times 10^{-4}$ mol | | | | $4 \times 10^{-4}$ mol | |
| N-(3,5-diamino-pyridin-2-yl)piperidine | | | | $4 \times 10^{-4}$ mol | | | | $4 \times 10^{-4}$ mol |
| 3-aminopyrazolo[1,5-a]pyridine dihydrochloride | $4 \times 10^{-4}$ mol | $4 \times 10^{-4}$ mol | $4 \times 10^{-4}$ mol | $4 \times 10^{-4}$ mol | | | | |
| 4,5-diamino-1-(2-hydroxyethyl)pyrazole dihydro-chloride | | | | | $4 \times 10^{-4}$ mol | $4 \times 10^{-4}$ mol | $4 \times 10^{-4}$ mol | $4 \times 10^{-4}$ mol |
| Dye support (1) | (*) | (*) | (*) | (*) | (*) | (*) | (*) | (*) |
| Demineralized water qs | 100 g | 100 g | 100 g | 100 g | 100 g | 100 g | 100 g | 100 g |

| | Examples | | | | | | | |
|---|---|---|---|---|---|---|---|---|
| | 17 | 18 | 19 | 20 | 21 | 22 | 23 | 24 |
| N-(3,5-diaminopyridin-2-yl)pyrrolidine | $4 \times 10^{-4}$ mol | | | | $4 \times 10^{-4}$ mol | | | |
| N-(3,5-diamino-pyridin-2-yl)-3-hydroxypyrrolidine | | $4 \times 10^{-4}$ mol | | | | $4 \times 10^{-4}$ mol | | |
| N-(3,5-diamino-pyridin-2-yl)-2-methylpyrrolidine | | | $4 \times 10^{-4}$ mol | | | | $4 \times 10^{-4}$ mol | |
| N-(3,5-diamino-pyridin-2-yl)piperidine | | | | $4 \times 10^{-4}$ mol | | | | $4 \times 10^{-4}$ mol |
| 1,3-bis(4,5-diaminopyrazol-1-yl)propane dihydrochloride | $4 \times 10^{-4}$ mol | $4 \times 10^{-4}$ mol | $4 \times 10^{-4}$ mol | $4 \times 10^{-4}$ mol | | | | |

-continued

| | | | | | | | | |
|---|---|---|---|---|---|---|---|---|
| 3-methyl-4,5-diamino-1-ethylpyrazole dihydrochloride | | | | | $4 \times 10^{-4}$ mol | $4 \times 10^{-4}$ mol | $4 \times 10^{-4}$ mol | $4 \times 10^{-4}$ mol |
| Dye support (1) | (*) | (*) | (*) | (*) | (*) | (*) | (*) | (*) |
| Demineralized water qs | 100 g | 100 g | 100 g | 100 g | 100 g | 100 g | 100 g | 100 g |

(*) Dye support (1) pH 7

| | |
|---|---|
| DMSO | 0.18 g |
| 96° Ethyl alcohol | 9.3 g |
| Methyl alcohol | 39.7 g |
| Acetic acid | 4.4 g |
| Sodium metabisulphite | 0.204 g |
| Pentasodium salt of diethylenetriaminepentacetic acid as an aqueous 40% solution | 1.1 g |
| $C_8$–$C_{15}$ alkyl polyglucoside sold as a 60% solution under the name Oramix CG110 by the company SEPPIC | 5.3 g |
| Benzyl alcohol | 1.8 g |
| Polyethylene glycol containing 8 mol of EO | 2.7 g |
| 0.5 M ammonium chloride buffer pH 7 | 31.0 g |

At the time of use, each composition was mixed with one third of its weight of 20-volumes aqueous hydrogen peroxide solution (6% by weight).

Each mixture obtained was applied to a lock of grey hair containing 90% white hairs. After a leave-in time of 30 minutes, the locks were rinsed, washed with a standard shampoo, rinsed again and then dried.

The following dyeing results were obtained:

| | Example | | | |
|---|---|---|---|---|
| | 1 | 2 | 3 | 4 |
| Shade observed | Grey | Dark violet | Grey | Grey |

| | Example | | | |
|---|---|---|---|---|
| | 9 | 10 | 11 | 12 |
| Shade observed | Violet-grey | Violet-grey | Violet-grey | Violet-grey |

| | Example | | | |
|---|---|---|---|---|
| | 17 | 18 | 19 | 20 |
| Shade observed | Bluish-violet grey | Blue-grey | Violet-grey | Light grey |

| | Example | | | |
|---|---|---|---|---|
| | 5 | 6 | 7 | 8 |
| Shade observed | Grey | Blue-grey | Grey | Grey |

| | Example | | | |
|---|---|---|---|---|
| | 13 | 14 | 15 | 16 |
| Shade observed | Grey | Grey | Violet | Blue-violet |

| | Example | | | |
|---|---|---|---|---|
| | 21 | 22 | 23 | 24 |
| Shade observed | Violet-grey | Violet-grey | Grey | Grey |

Examples B of Dyeing in Alkaline Medium

Examples 1 to 7

The following dye compositions were prepared:

| | Example | | | | | | |
|---|---|---|---|---|---|---|---|
| | 1 | 2 | 3 | 4 | 5 | 6 | 7 |
| Compound of Example 7 | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | | |
| Benzene-1,4-diamine hydrochloride | | $10^{-3}$ mol | | | | | |
| 2-[(4-Aminophenyl)(2-hydroxyethyl)amino]ethanol sulphate | | | $10^{-3}$ mol | | | | |
| Pyrimidine-2,4,5,6-tetraamine sulphate | | | | $10^{-3}$ mol | | | |
| 2-Ethyl-5-methyl-2H-pyrazole-3,4-diamine hydrochloride | | | | | $10^{-3}$ mol | | |
| 5-Methylpyrazolo[1,5-a]pyrimidine-3,7-diamine hydrochloride | | | | | | $10^{-3}$ mol | |
| 2-(4,5-Diaminopyrazol-1-yl)ethanol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*) Dye support (1) pH 9.5

| | |
|---|---|
| 96° Ethyl alcohol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition was mixed at the time of use with an equal weight of 20-volumes aqueous hydrogen peroxide solution (6% by weight). A final pH of 9.5 was obtained.

Each mixture obtained was applied to grey hair containing 90% white hairs. After a leave-in time of 30 minutes, the hair was rinsed, washed with a standard shampoo, rinsed again and then dried.

The following dyeing results were obtained:

| | Example | | | | | | |
|---|---|---|---|---|---|---|---|
| | 1 | 2 | 3 | 4 | 5 | 6 | 7 |
| Shade observed | orange | strong grey | strong blue-green | strong grey | strong violet-grey | strong violet | strong violet-grey |

Examples 8 and 9

The following dye compositions were prepared:

| | Example | |
|---|---|---|
| | 8 | 9 |
| Compound of Example 13 | $10^{-3}$ mol | $10^{-3}$ mol |
| 2-[(4-Aminophenyl)(2-hydroxyethyl)-amino]ethanol sulphate | $10^{-3}$ mol | |
| Pyrimidine-2,4,5,6-tetraamine sulphate | | $10^{-3}$ mol |
| Dye support (1) | (*) | (*) |
| Demineralized water qs | 100 g | 100 g |

See the composition of the dye support (1) pH 9.5 and the application in Examples 1 to 7.

The following dyeing results were obtained:

| | Example | |
|---|---|---|
| | 8 | 9 |
| Shade observed | strong blue-green | strong violet-grey |

Examples 10 to 15

The following dye compositions were prepared:

| | Example | | | | | |
|---|---|---|---|---|---|---|
| | 10 | 11 | 12 | 13 | 14 | 15 |
| Compound of Example 11 | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | |
| Benzene-1,4-diamine hydrochloride | | $10^{-3}$ mol | | | | |
| 2-[(4-Aminophenyl)(2-hydroxyethyl)-amino]ethanol sulphate | | | $10^{-3}$ mol | | | |
| Pyrimidine-2,4,5,6-tetraamine sulphate | | | | $10^{-3}$ mol | | |
| 5-Methylpyrazolo[1,5-a]pyrimidine-3,7-diamine hydrochloride | | | | | $10^{-3}$ mol | |
| 2-(4,5-Diaminopyrazol-1-yl)ethanol hydrochloride | | | | | | $10^{-3}$ mol |
| Dye support (1) | (*) | (*) | (*) | (*) | (*) | (*) |
| Demineralized water qs | 100 g | 100 g | 100 g | 100 g | 100 g | 100 g |

See the composition of the dye support (1) pH 9.5 and the application in Examples 1 to 7.

The following dyeing results were obtained:

| | Example | | | | | |
|---|---|---|---|---|---|---|
| | 10 | 11 | 12 | 13 | 14 | 15 |
| Shade observed | orange | strong grey | strong green | strong grey | strong violet-grey | strong violet-grey |

Examples 16 to 18

The following dye compositions were prepared:

| | Example | | |
|---|---|---|---|
| | 16 | 17 | 18 |
| Compound of Example 12 | $10^{-3}$ mol | $10^{-3}$ mol | $10^{-3}$ mol |
| 2-[(4-Aminophenyl)(2-hydroxyethyl)amino]ethanol sulphate | $10^{-3}$ mol | | |
| Pyrimidine-2,4,5,6-tetraamine sulphate | | $10^{-3}$ mol | |
| 2-(4,5-Diaminopyrazol-1-yl)ethanol hydrochloride | | | $10^{-3}$ mol |
| Dye support (1) | (*) | (*) | (*) |
| Demineralized water qs | 100 g | 100 g | 100 g |

See the composition of the dye support (1) pH 9.5 and the application in Examples 1 to 7.

The following dyeing results were obtained:

| | Example | | |
|---|---|---|---|
| | 16 | 17 | 18 |
| Shade observed | strong blue-green | strong grey | strong violet-grey |

Examples 19 to 21

The following dye compositions were prepared:

| | Example | | |
|---|---|---|---|
| | 19 | 20 | 21 |
| Compound of Example 8 | $10^{-3}$ mol | $10^{-3}$ mol | $10^{-3}$ mol |
| 2-[(4-Aminophenyl)(2-hydroxyethyl)amino]ethanol sulphate | $10^{-3}$ mol | | |
| Pyrimidine-2,4,5,6-tetraamine sulphate | | $10^{-3}$ mol | |
| 2-(4,5-Diaminopyrazol-1-yl)ethanol hydrochloride | | | $10^{-3}$ mol |
| Dye support (1) | (*) | (*) | (*) |
| Demineralized water qs | 100 g | 100 g | 100 g |

See the composition of the dye support (1) pH 9.5 and the application in Examples 1 to 7.

The following dyeing results were obtained:

|  | Example | | |
|---|---|---|---|
|  | 19 | 20 | 21 |
| Shade observed | strong blue-green | strong blue-green grey | strong violet-grey |

Examples 22 to 28

The following dye compositions were prepared:

|  | Example | | | | | | |
|---|---|---|---|---|---|---|---|
|  | 22 | 23 | 24 | 25 | 26 | 27 | 28 |
| Compound of Example 9 | $10^{-3}$ mol | $10^{-3}$ mol | $10^{-3}$ mol | $10^{-3}$ mol | $10^{-3}$ mol | $10^{-3}$ mol |  |
| 4-Aminophenol | $10^{-3}$ mol |  |  |  |  |  |  |
| Benzene-1,4-diamine hydrochloride |  | $10^{-3}$ mol |  |  |  |  |  |
| 2-[(4-Aminophenyl)(2-hydroxyethyl)-amino]ethanol sulphate |  |  | $10^{-3}$ mol |  |  |  |  |
| Pyrimidine-2,4,5,6-tetraamine sulphate |  |  |  | $10^{-3}$ mol |  |  |  |
| 2-Ethyl-5-methyl-2H-pyrazole-3,4-diamine hydrochloride |  |  |  |  | $10^{-3}$ mol |  |  |
| 5-Methylpyrazolo[1,5-a]pyrimidine-3,7-diamine hydrochloride |  |  |  |  |  | $10^{-3}$ mol |  |
| 2-(4,5-Diamino-pyrazol-1-yl)ethanol hydrochloride |  |  |  |  |  |  | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

See the composition of the dye support (1) pH 9.5 and the application in Examples 1 to 7.

The following dyeing results were obtained:

|  | Example | | | | | | |
|---|---|---|---|---|---|---|---|
|  | 22 | 23 | 24 | 25 | 26 | 27 | 28 |
| Shade observed | red grey | strong grey | strong green | strong grey | strong grey | strong red-grey | strong red-violet grey |

Examples 29 to 34

The following dye compositions were prepared:

|  | Example | | | | | |
|---|---|---|---|---|---|---|
|  | 29 | 30 | 31 | 32 | 33 | 34 |
| Compound of Example 10 | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol |  |  |  |  |  |
| Benzene-1,4-diamine hydrochloride |  | $10^{-3}$ mol |  |  |  |  |
| 2-[(4-Aminophenyl)(2-hydroxyethyl)amino]ethanol sulphate |  |  | $10^{-3}$ mol |  |  |  |
| Pyrimidine-2,4,5,6-tetraamine sulphate |  |  |  | $10^{-3}$ mol |  |  |
| 5-Methylpyrazolo[1,5-a]pyrimidine-3,7-diamine hydrochloride |  |  |  |  | $10^{-3}$ mol |  |
| 2-(4,5-Diaminopyrazol-1-yl)ethanol hydrochloride |  |  |  |  |  | $10^{-3}$ mol |
| Dye support (1) | (*) | (*) | (*) | (*) | (*) | (*) |
| Demineralized water qs | 100 g | 100 g | 100 g | 100 g | 100 g | 100 g |

See the composition of the dye support (1) pH 9.5 and the application in Examples 1 to 7.

The following dyeing results were obtained:

|  | Example | | | | | |
|---|---|---|---|---|---|---|
|  | 29 | 30 | 31 | 32 | 33 | 34 |
| Shade observed | orange | strong grey | strong blue-green | grey | strong violet-grey | strong violet-grey |

Examples C of Dyeing in Acid Medium

Examples 35 to 40

The following dye compositions were prepared:

|  | Example | | | | | |
|---|---|---|---|---|---|---|
|  | 35 | 36 | 37 | 38 | 39 | 40 |
| Compound of Example 7 | $10^{-3}$ mol | $10^{-3}$ mol | $10^{-3}$ mol | $10^{-3}$ mol | $10^{-3}$ mol | $10^{-3}$ mol |
| Benzene-1,4-diamine hydrochloride | $10^{-3}$ mol |  |  |  |  |  |
| 2-[(4-Aminophenyl)(2-hydroxyethyl)amino]-ethanol sulphate |  | $10^{-3}$ mol |  |  |  |  |
| Pyrimidine-2,4,5,6-tetraamine sulphate |  |  | $10^{-3}$ mol |  |  |  |
| 2-Ethyl-5-methyl-2H-pyrazole-3,4-diamine hydrochloride |  |  |  | $10^{-3}$ mol |  |  |
| 5-Methylpyrazolo[1,5-a]pyrimidine-3,7-diamine hydrochloride |  |  |  |  | $10^{-3}$ mol |  |
| 2-(4,5-Diaminopyrazol-1-yl)ethanol hydrochloride |  |  |  |  |  | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*) Dye support (2) pH 7

| | |
|---|---|
| 96° Ethyl alcohol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition was mixed at the time of use with an equal weight of 20-volumes aqueous hydrogen peroxide solution (6% by weight). A final pH of 7 was obtained.

Each mixture obtained was applied to grey hair containing 90% white hairs. After a leave-in time of 30 minutes, the hair was rinsed, washed with a standard shampoo, rinsed again and then dried.

The following dyeing results were obtained:

| | Example | | | | | |
|---|---|---|---|---|---|---|
| | 35 | 36 | 37 | 38 | 39 | 40 |
| Shade observed | strong blue-green grey | strong blue-green | strong blue-violet grey | strong violet-grey | strong violet | strong violet-grey |

Examples 41 to 43

The following dye compositions were prepared:

| | Example | | |
|---|---|---|---|
| | 41 | 42 | 43 |
| Compound of Example 13 | $10^{-3}$ mol | $10^{-3}$ mol | $10^{-3}$ mol |
| 4-Aminophenol | $10^{-3}$ mol | | |
| 2-[(4-Aminophenyl)(2-hydroxyethyl)amino]ethanol sulphate | | $10^{-3}$ mol | |
| Pyrimidine-2,4,5,6-tetraamine sulphate | | | $10^{-3}$ mol |
| Dye support (2) | (*) | (*) | (*) |
| Demineralized water qs | 100 g | 100 g | 100 g |

See the composition of the dye support (2) pH 7 and the application in Examples 35 to 40.

The following dyeing results were obtained:

| | Example | | |
|---|---|---|---|
| | 41 | 42 | 43 |
| Shade observed | strong orange-brown | strong blue-green grey | strong grey |

Examples 44 to 50

The following dye compositions were prepared:

| | Example | | | | | | |
|---|---|---|---|---|---|---|---|
| | 44 | 45 | 46 | 47 | 48 | 49 | 50 |
| Compound of Example 11 | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | | |
| Benzene-1,4-diamine hydrochloride | | $10^{-3}$ mol | | | | | |
| 2-[(4-Aminophenyl)(2-hydroxyethyl)amino]ethanol sulphate | | | $10^{-3}$ mol | | | | |
| Pyrimidine-2,4,5,6-tetraamine sulphate | | | | $10^{-3}$ mol | | | |
| 2-Ethyl-5-methyl-2H-pyrazole-3,4-diamine hydrochloride | | | | | $10^{-3}$ mol | | |
| 5-Methylpyrazolo[1,5-a]pyrimidine-3,7-diamine hydrochloride | | | | | | $10^{-3}$ mol | |
| 2-(4,5-Diamino-pyrazol-1-yl)ethanol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

See the composition of the dye support (2) pH 7 and the application in Examples 35 to 40.

The following dyeing results were obtained:

| | Example | | | | | | |
|---|---|---|---|---|---|---|---|
| | 44 | 45 | 46 | 47 | 48 | 49 | 50 |
| Shade observed | orange | strong grey | strong blue-green | strong grey | strong violet-grey | strong violet-grey | strong violet-grey |

Examples 51 to 54

The following dye compositions were prepared:

| | Example | | | |
|---|---|---|---|---|
| | 51 | 52 | 53 | 54 |
| Compound of Example 12 | $10^{-3}$ mol | $10^{-3}$ mol | $10^{-3}$ mol | $10^{-3}$ mol |
| Benzene-1,4-diamine hydrochloride | $10^{-3}$ mol | | | |
| 2-[(4-Aminophenyl)(2-hydroxyethyl)amino]ethanol sulphate | | $10^{-3}$ mol | | |
| Pyrimidine-2,4,5,6-tetraamine sulphate | | | $10^{-3}$ mol | |
| 2-(4,5-Diaminopyrazol-1-yl)ethanol hydrochloride | | | | $10^{-3}$ mol |
| Dye support (2) | (*) | (*) | (*) | (*) |
| Demineralized water qs | 100 g | 100 g | 100 g | 100 g |

See the composition of the dye support (2) pH 7 and the application in Examples 35 to 40.

The following dyeing results were obtained:

|  | Example | | | |
|---|---|---|---|---|
|  | 51 | 52 | 53 | 54 |
| Shade observed | strong grey | strong blue-green | strong grey | strong violet-grey |

Examples 55 to 61

The following dye compositions were prepared:

| | Example | | | | | | |
|---|---|---|---|---|---|---|---|
| | 55 | 56 | 57 | 58 | 59 | 60 | 61 |
| Compound of Example 8 | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | | |
| Benzene-1,4-diamine hydrochloride | | $10^{-3}$ mol | | | | | |
| 2-[(4-Aminophenyl)(2-hydroxyethyl)amino]-ethanol sulphate | | | $10^{-3}$ mol | | | | |
| Pyrimidine-2,4,5,6-tetraamine sulphate | | | | $10^{-3}$ mol | | | |
| 2-Ethyl-5-methyl-2H-pyrazole-3,4-diamine hydrochloride | | | | | $10^{-3}$ mol | | |
| 5-Methylpyrazolo[1,5-a]pyrimidine-3,7-diamine hydrochloride | | | | | | $10^{-3}$ mol | |
| 2-(4,5-Diamino-pyrazol-1-yl)ethanol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

See the composition of the dye support (2) pH 7 and the application in Examples 35 to 40.

The following dyeing results were obtained:

| | Example | | | | | | |
|---|---|---|---|---|---|---|---|
| | 55 | 56 | 57 | 58 | 59 | 60 | 61 |
| Shade observed | orange | strong blue-green grey | strong blue-green | strong grey | strong grey | strong violet-grey | strong violet-grey |

Examples 62 to 68

The following dye compositions were prepared:

| | Example | | | | | | |
|---|---|---|---|---|---|---|---|
| | 62 | 63 | 64 | 65 | 66 | 67 | 68 |
| Compound of Example 9 | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | | |
| Benzene-1,4-diamine hydrochloride | | $10^{-3}$ mol | | | | | |
| 2-[(4-Aminophenyl)(2-hydroxyethyl)amino]-ethanol sulphate | | | $10^{-3}$ mol | | | | |
| Pyrimidine-2,4,5,6-tetraamine sulphate | | | | $10^{-3}$ mol | | | |
| 2-Ethyl-5-methyl-2H-pyrazole-3,4-diamine hydrochloride | | | | | $10^{-3}$ mol | | |
| 5-Methylpyrazolo[1,5-a]pyrimidine-3,7-diamine hydrochloride | | | | | | $10^{-3}$ mol | |
| 2-(4,5-Diamino-pyrazol-1-yl)ethanol hydrochloride | | | | | | | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

See the composition of the dye support (2) pH 7 and the application in Examples 35 to 40.

The following dyeing results were obtained:

| | Example | | | | | | |
|---|---|---|---|---|---|---|---|
| | 62 | 63 | 64 | 65 | 66 | 67 | 68 |
| Shade observed | orange | strong grey | strong blue-green grey | strong grey | strong grey | strong red-violet grey | strong red-violet grey |

Examples 69 to 74

The following dye compositions were prepared:

| | Example | | | | | |
|---|---|---|---|---|---|---|
| | 69 | 70 | 71 | 72 | 73 | 74 |
| Compound of Example 10 | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | | | | | |
| Benzene-1,4-diamine hydrochloride | | $10^{-3}$ mol | | | | |
| 2-[(4-Aminophenyl)(2-hydroxyethyl)-amino]ethanol sulphate | | | $10^{-3}$ mol | | | |
| Pyrimidine-2,4,5,6-tetra-amine sulphate | | | | $10^{-3}$ mol | | |
| 2-Ethyl-5-methyl-2H-pyrazole-3,4-diamine hydrochloride | | | | | $10^{-3}$ mol | |
| 2-(4,5-Diaminopyrazol-1-yl)ethanol hydrochloride | | | | | | $10^{-3}$ mol |
| Dye support (2) | (*) | (*) | (*) | (*) | (*) | (*) |
| Demineralized water qs | 100 g | 100 g | 100 g | 100 g | 100 g | 100 g |

See the composition of the dye support (2) pH 7 and the application in Examples 35 to 40.

The following dyeing results were obtained:

| | Example | | | | | |
|---|---|---|---|---|---|---|
| | 69 | 70 | 71 | 72 | 73 | 74 |
| Shade observed | orange | strong grey | strong blue-green | strong grey | strong grey | strong violet-grey |

What is claimed is:

1. A dye composition comprising, in a medium that is suitable for dyeing:
  at least one oxidation base, and
  at least one 2,3,5-triaminopyridine coupler of formula (I), or a corresponding addition salt thereof:

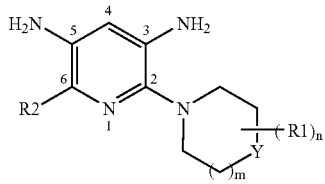

Formula (I)

wherein:
$R_1$ is chosen from:
  a halogen atom;
  a $C_1$–$C_4$ alkyl radical optionally substituted with at least one radical chosen from hydroxyl, carboxyl, ($C_1$–$C_4$) alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals
  a carboxyl radical;
  a ($C_1$–$C_4$)alkoxycarbonyl radical;
  a carboxamido radical;
  a ($C_1$–$C_4$)alkylcarboxamido radical;
  a sulphinic radical;
  a $C_1$–$C_4$ alkylsulphonyl radical;
  a $C_1$–$C_4$ alkylsulphonamido radical;
  a hydroxyl radical;
  a $C_1$–$C_4$ alkoxy radical;
  a $C_2$–$C_4$ hydroxyalkoxy radical;
  a radical chosen from amino, monoaminoalkoxy and diaminoalkoxy radicals;
  a $C_1$–$C_4$ thioether radical;
  a $C_1$–$C_4$ alkylsulphoxy radical;
  a sulphonic radical; and
  a radical $NR_5R_6$;
$R_3$, $R_4$, $R_5$ and $R_6$, which may be identical or different, are chosen from a hydrogen atom; a $C_1$–$C_4$ alkylsulphonyl radical; a ($C_1$–$C_4$) alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and (di)($C_1$–$C_4$) alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, (di)($C_1$–$C_4$)alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals,
n ranges from 0 to 7,
m is 0, 1 or 2,
Y is chosen from an oxygen atom, a radical $C(R_8)_2$ and a radical $NR_7$ in which $R_7$ has the same meaning as $R_3$, and
$R_8$, which may be identical or different, is chosen from a hydrogen atom or has the same meaning as $R_1$.

2. The composition according to claim 1, wherein $R_1$ is chosen from a $C_1$–$C_4$ alkoxy radical optionally substituted with at least one radical chosen from hydroxyl, $C_1$–$C_2$ alkoxy, amino and (di)alkylamino radicals; a hydroxyl radical; an amino radical; (di)alkylamino radicals; and a $C_1$–$C_2$ alkyl radical optionally substituted with a radical chosen from hydroxyl and amino radicals.

3. The composition according to claim 1, wherein $R_2$ is chosen from a hydrogen atom and an alkoxy radical.

4. The composition according to claim 1, wherein n is chosen from 0 or 1.

5. The composition according to claim 1, wherein $R_3$, $R_4$, $R_5$, $R_6$ and $R_7$, which may be identical or different, are chosen from a hydrogen atom, a carboxamido radical, a $C_1$–$C_4$ alkyl radical optionally substituted with at least one radical chosen from hydroxyl, $C_1$–$C_4$ alkoxy, carboxamido, amino, (di)($C_1$–$C_4$)alkylamino and $C_2$–$C_4$ (poly)hydroxyalkylamino radicals.

6. The composition according to claim 1, wherein $R_3$, $R_4$, $R_5$, $R_6$ and $R_7$, which may be identical or different, are chosen from a hydrogen atom and from methyl, ethyl, 2-carboxyethyl, 2-hydroxyethyl, 3-hydroxypropyl, 2,3-dihydroxypropyl, 2-hydroxy-3-aminopropyl and 3-hydroxy-2-aminopropyl radicals.

7. The composition according to claim 6, wherein $R_3$, $R_4$, $R_5$, $R_6$ and $R_7$, which may be identical or different, are chosen from a hydrogen atom, a methyl radical, a 2-hydroxyethyl radical and a 2,3-dihydroxypropyl radical.

8. The composition according to claim 1, wherein the nitrogen in position 2 of the ring, together with Y and m, form a heterocyclic radical chosen from pyrrolidines, piperidines, homopiperidines, piperazines, homopiperazines and diazepanes.

9. The composition according to claim 8, wherein the heterocycle is chosen from pyrrolidine, 2,5-dimethylpyrrolidine, 2-methylpyrrolidine, proline, 3-hydroxyproline, 4-hydroxyproline, 2,4-dicarboxypyrrolidine, 2-hydroxymethylpyrrolidine, 3-hydroxy-2-hydroxymethylpyrrolidine, 2,5-di(hydroxymethyl)-pyrrolidine, 2-carboxamidopyrrolidine, 3-hydroxy-2-carboxamidopyrrolidine, 2-(dimethylcarboxamido)-pyrrolidine, 2-(dimethylcarboxamido)-3-hydroxypyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 4-methylamino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-(dimethylcarboxamido) piperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, piperazine, 4-methylpiperazine, diazepane, N-methyl-homopiperazine and N-β-hydroxyethylhomopiperazine, and the addition salts thereof.

10. The composition according to claim 8, wherein the heterocycle is chosen from pyrrolidine, 2-methylpyrrolidine, 3-hydroxypyrrolidine, 3-aminopyrrolidine, 3-(methylsulphonylamino)pyrroline, proline, 3-hydroxyproline, piperidine, hydroxypiperidine, homopiperidine, 4-methylpiperazine, diazepane, N-methylhomopiperazine and N-β-hydroxyethylhomopiperazine, and the addition salts thereof.

11. The composition according to claim 10, wherein the heterocycle is chosen from pyrrolidine, 3-hydroxypyrrolidine, 3-aminopyrrolidine, 3-(methyl-sulphonylamino)pyrrolidine, proline, and 3-hydroxyproline.

12. The composition according to claim 1, wherein $R_1$ is chosen from alkyl, amino, hydroxyalkyl and hydroxyl radicals, $R_2$ is hydrogen, m is 0 or 1, and n is 0, 1 or 2.

13. The composition according to claim 1, wherein the at least one 2,3,5,-triaminopyridine coupler of formula (I) is chosen from:
N-(3,5-diaminopyrid-2-yl)pyrrolidine;
N-(3,5-diaminopyrid-2-yl)-2-methylpyrrolidine;
N-(3,5-diaminopyrid-2-yl)-2,5-dimethylpyrrolidine;
N-(3,5-diaminopyrid-2-yl)-2-hydroxymethylpyrrolidine;
N-(3,5-diaminopyrid-2-yl)proline;
N-(3,5-diaminopyrid-2-yl)-3-hydroxypyrrolidine;
N-(3,5-diaminopyrid-2-yl)-2-carboxamidopyrrolidine;
N-(3,5-diaminopyrid-2-yl)-2-dimethylcarboxamidopyrrolidine;
N-(3,5-diaminopyrid-2-yl)-3,4-dihydroxypyrrolidine;
N-(3,5-diaminopyrid-2-yl)-3-aminopyrrolidine;
N-(3,5-diaminopyrid-2-yl)-3-dimethylaminopyrrolidine;
N-(3,5-diaminopyrid-2-yl)piperidine;
N-(3,5-diaminopyrid-2-yl)-4-methylpiperazine; and
the addition salts thereof.

14. The composition according to claim 1, wherein the at least one oxidation base is chosen from para-phenylenediamines, bis(phenyl)alkylenediamines, para-aminophenols, ortho-aminophenols and heterocyclic bases, and the addition salts thereof.

15. The composition according to claim 1, wherein the at least one oxidation base is present in an amount ranging from 0.001% to 10% by weight relative to the total weight of the dye composition.

16. The composition according to claim 1, wherein the at least one oxidation base is present in an amount ranging from 0.005% to 6% by weight relative to the total weight of the dye composition.

17. The composition according to claim 1, comprising at least one additional coupler chosen from meta-phenylenediamines, meta-aminophenols, meta-diphenols, naphthalene-based couplers and heterocyclic couplers other than the couplers of formula (I), and the addition salts thereof.

18. The composition according to claim 1, wherein the at least one 2,3,5-triaminopyridine coupler and any additional couplers, if present, are present in a total amount ranging from 0.001% to 10% by weight relative to the total weight of the dye composition.

19. The composition according to claim 1, wherein the at least one 2,3,5-triaminopyridine coupler and any additional couplers, if any, are present in a total amount ranging from 0.005% to 6% by weight relative to the total weight of the dye composition.

20. The composition according to claim 1, wherein the dyeing medium is a cosmetic medium that is suitable for dyeing keratin fibers.

21. The composition according to claim 1, further comprising an oxidizing agent.

22. A process for the oxidation dyeing of keratin fibers, comprising applying a dye composition to said keratin fibers, in the presence of at least one oxidizing agent, for a time allowing a desired color to be obtained, wherein said dye composition comprises, in a medium that is suitable for dyeing:
at least one oxidation base, and
at least one 2,3,5-triaminopyridine coupler of formula (I), or a corresponding addition salt thereof:

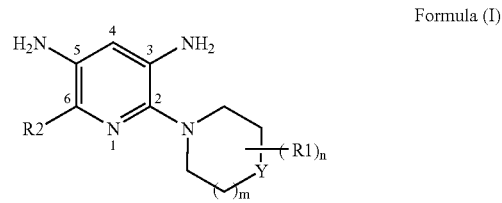

Formula (I)

wherein:
$R_1$ is chosen from:
  a halogen atom;
  a $C_1$–$C_4$ alkyl radical optionally substituted with at least one radical chosen from hydroxyl, carboxyl, ($C_1$–$C_4$) alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
  a carboxyl radical;
  a ($C_1$–$C_4$)alkoxycarbonyl radical;
  a carboxamido radical;
  a ($C_1$–$C_4$)alkylcarboxamido radical;
  a sulphinic radical;
  a $C_1$–$C_4$ alkylsulphonyl radical;
  a $C_1$–$C_4$ alkylsulphonamido radical;
  a hydroxyl radical;
  a $C_1$–$C_4$ alkoxy radical;
  a $C_2$–$C_4$ hydroxyalkoxy radical;
  a radical chosen from amino, monoaminoalkoxy and diaminoalkoxy radicals;
  a $C_1$–$C_4$ thioether radical;
  a $C_1$–$C_4$ alkylsulphoxy radical;
  a sulphonic radical; and
  a radical $NR_5R_6$;
$R_3$, $R_4$, $R_5$ and $R_6$, which may be identical or different, are chosen from a hydrogen atom; a $C_1$–$C_4$ alkylsulphonyl radical; a ($C_1$–$C_4$) alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and (di)($C_1$–$C_4$) alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, (di)($C_1$–$C_4$)alkylamino and $C_2$–$C_4$ (poly)hydroxyalkylamino radicals;
$R_2$ is chosen from a hydrogen atom, a $C_1$–$C_4$ alkoxy radical optionally substituted with at least one radical chosen from hydroxyl and $C_1$–$C_2$ alkoxy radicals,
n ranges from 0 to 7,
m is 0, 1 or 2,
Y is chosen from an oxygen atom, a radical $C(R_8)_2$ and a radical $NR_7$ in which $R_7$ has the same meaning as $R_3$, and
$R_8$, which may be identical or different, is chosen from a hydrogen atom or has the same meaning as $R_1$.

23. The process according to claim 22, wherein the at least one oxidizing agent is chosen from hydrogen peroxide, urea peroxide, alkali metal bromates, persalts, peracids and oxidase enzymes.

24. The process according to claim 22, wherein the at least one oxidizing agent is mixed at the time of use with the dye composition.

25. The process according to claim 22, wherein the at least one oxidizing agent is applied to the fibers simultaneously with or sequentially to the dye composition, in the form of an oxidizing composition.

26. A multi-compartment kit comprising a first compartment comprising a dye composition comprising, in a medium that is suitable for dyeing:
at least one oxidation base, and
at least one 2,3,5-triaminopyridine coupler of formula (I), or a corresponding addition salt thereof:

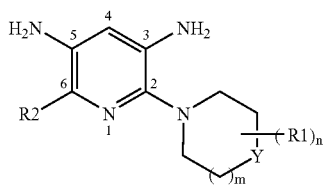

Formula (I)

wherein:
$R_1$ is chosen from:
a halogen atom;
a $C_1$–$C_4$ alkyl radical optionally substituted with at least one radical chosen from hydroxyl, carboxyl, ($C_1$–$C_4$) alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
a carboxyl radical;
a ($C_1$–$C_4$)alkoxycarbonyl radical;
a carboxamido radical;
a ($C_1$–$C_4$)alkylcarboxamido radical;
a sulphinic radical;
a $C_1$–$C_4$ alkylsulphonyl radical;
a $C_1$–$C_4$ alkylsulphonamido radical;
a hydroxyl radical;
a $C_1$–$C_4$ alkoxy radical;
a $C_2$–$C_4$ hydroxyalkoxy radical;
a radical chosen from amino, monoaminoalkoxy and diaminoalkoxy radicals;
a $C_1$–$C_4$ thioether radical;
a $C_1$–$C_4$ alkylsulphoxy radical;
a sulphonic radical; and
a radical $NR_5R_6$;
$R_3$, $R_4$, $R_5$ and $R_6$, which may be identical or different, are chosen from a hydrogen atom; a $C_1$–$C_4$ alkylsulphonyl radical; a ($C_1$–$C_4$) alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and (di)($C_1$–$C_4$) alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, (di)($C_1$–$C_4$)alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals,
n ranges from 0 to 7,
m is 0, 1 or 2,
Y is chosen from an oxygen atom, a radical $C(R_8)_2$ and a radical $NR_7$ in which $R_7$ has the same meaning as $R_3$, and
$R_8$, which may be identical or different, is chosen from a hydrogen atom or has the same meaning as $R_3$, and
a second compartment comprising an oxidizing composition.

27. A kit for dyeing keratin fibers comprising a dye composition comprising, in a medium that is suitable for dyeing:
at least one oxidation base, and
at least one 2,3,5-triaminopyridine coupler of formula (I), or a corresponding addition salt thereof:

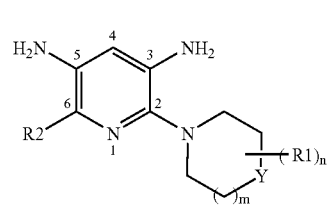

Formula (I)

wherein:
$R_1$ is chosen from:
a halogen atom;
a $C_1$–$C_4$ alkyl radical optionally substituted with at least one radical chosen from hydroxyl, carboxyl, ($C_1$–$C_4$) alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
a carboxyl radical;
a ($C_1$–$C_4$)alkoxycarbonyl radical;
a carboxamido radical;
a ($C_1$–$C_4$)alkylcarboxamido radical;
a sulphinic radical;
a $C_1$–$C_4$ alkylsulphonyl radical;
a $C_1$–$C_4$ alkylsulphonamido radical;
a hydroxyl radical;
a $C_1$–$C_4$ alkoxy radical;
a $C_2$–$C_4$ hydroxyalkoxy radical;
a radical chosen from amino, monoaminoalkoxy and diaminoalkoxy radicals;
a $C_1$–$C_4$ thioether radical;
a $C_1$–$C_4$ alkylsulphoxy radical;
a sulphonic radical; and
a radical $NR_5R_6$;
$R_3$, $R_4$, $R_5$ and $R_6$, which may be identical or different, are chosen from a hydrogen atom; a $C_1$–$C_4$ alkylsulphonyl radical; a ($C_1$–$C_4$) alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and (di)($C_1$–$C_4$) alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, (di)($C_1$–$C_4$)alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals, n ranges from 0 to 7, m is 0, 1 or 2, Y is chosen from an oxygen atom, a radical $C(R_8)_2$ and a radical $NR_7$ in which $R_7$ has the same meaning as $R_3$, and $R_8$, which may be identical or different, is chosen from a hydrogen atom or has the same meaning as $R_1$, and an oxidizing composition.

28. A 2,3,5-Triaminopyridine compound of formula (I)

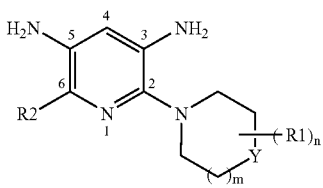

Formula (I)

wherein:

$R_1$ is chosen from:
- a halogen atom;
- a $C_1$–$C_4$ alkyl radical optionally substituted with at least one radical chosen from hydroxyl, carboxyl, $(C_1$–$C_4)$ alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
- a carboxyl radical;
- a $(C_1$–$C_4)$alkoxycarbonyl radical;
- a carboxamido radical;
- a $(C_1$–$C_4)$alkylcarboxamido radical;
- a sulphinic radical;
- a $C_1$–$C_4$ alkylsulphonyl radical;
- a $C_1$–$C_4$ alkylsulphonamido radical;
- a hydroxyl radical;
- a $C_1$–$C_4$ alkoxy radical;
- a $C_2$–$C_4$ hydroxyalkoxy radical;
- a radical chosen from amino, monoaminoalkoxy and diaminoalkoxy radicals;
- a $C_1$–$C_4$ thioether radical;
- a $C_1$–$C_4$ alkylsulphoxy radical;
- a sulphonic radical; and
- a radical $NR_5R_6$;

$R_3$, $R_4$, $R_5$ and $R_6$, which may be identical or different, are chosen from a hydrogen atom; a $C_1$–$C_4$ alkylsulphonyl radical; a $(C_1$–$C_4)$ alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and $(di)(C_1$–$C_4)$ alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, $(di)(C_1$–$C_4)$alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals, n ranges from 0 to 7, m is 0, 1 or 2, Y is chosen from an oxygen atom, a radical $C(R_8)_2$ and a radical $NR_7$ in which $R_7$ has the same meaning as $R_3$, and $R_8$, which may be identical or different, is chosen from a hydrogen atom or has the same meaning as $R_1$.

29. A nitro compound of formula (II)

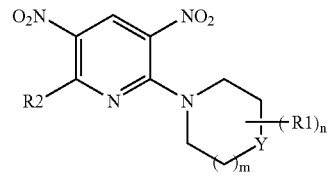

wherein:

$R_1$ is chosen from:
- a halogen atom;
- a $C_1$–$C_4$ alkyl radical optionally substituted with at least one radical chosen from hydroxyl, carboxyl, $(C_1$–$C_4)$ alkoxycarbonyl, carboxamido, $C_1$–$C_4$ alkylsulphonyl, $C_1$–$C_4$ alkoxy, $C_1$–$C_4$ alkylsulphonamido and $NR_3R_4$ radicals;
- a carboxyl radical;
- a $(C_1$–$C_4)$alkoxycarbonyl radical;
- a carboxamido radical;
- a $(C_1$–$C_4)$alkylcarboxamido radical;
- a sulphinic radical;
- a $C_1$–$C_4$ alkylsulphonyl radical;
- a $C_1$–$C_4$ alkylsulphonamido radical;
- a hydroxyl radical;
- a $C_1$–$C_4$ alkoxy radical;
- a $C_2$–$C_4$ hydroxyalkoxy radical;
- a radical chosen from amino, monoaminoalkoxy and diaminoalkoxy radicals;
- a $C_1$–$C_4$ thioether radical;
- a $C_1$–$C_4$ alkylsulphoxy radical;
- a sulphonic radical; and
- a radical $NR_5R_6$;

$R_3$, $R_4$, $R_5$ and $R_6$, which may be identical or different, are chosen from a hydrogen atom; a $C_1$–$C_4$ alkylsulphonyl radical; a $(C_1$–$C_4)$ alkylcarbonyl radical in which the alkyl radical may be substituted with at least one hydroxyl radical; an arylcarbonyl radical, the aryl radical possibly being substituted with a radical chosen from hydroxyl, $C_1$–$C_4$ alkoxy, amino and $(di)(C_1$–$C_4)$ alkylamino; a carboxamido radical; a $C_1$–$C_4$ alkyl radical optionally substituted with at least one radical chosen from hydroxyl, $C_1$–$C_4$ alkoxy, $C_1$–$C_4$ alkylsulphonyl, $C_1$–$C_4$ alkylsulphonamido, carboxyl, carboxamido, $C_1$–$C_4$ alkylsulphoxy, amino, $(di)(C_1$–$C_4)$alkylamino and $C_2$–$C_4$ (poly)hydroxyalkylamino radicals;

$R_2$ is chosen from a hydrogen atom, a $C_1$–$C_4$ alkoxy radical optionally substituted with at least one radical chosen from hydroxyl and $C_1$–$C_2$ alkoxy radicals, n ranges from 0 to 7, m is 0, 1 or 2, Y is chosen from an oxygen atom, a radical $C(R_8)_2$ and a radical $NR_7$ in which $R_7$ has the same meaning as $R_3$, and $R_8$, which may be identical or different, is chosen from a hydrogen atom or has the same meaning as $R_1$ with the proviso that when Y is $NR_7$, where $R_7$ is a hydrogen atom, n is 0 and m is 1, $R_2$ is not a hydrogen atom.

* * * * *

UNITED STATES PATENT AND TRADEMARK OFFICE
CERTIFICATE OF CORRECTION

PATENT NO. : 7,175,670 B2
APPLICATION NO. : 10/798454
DATED : February 13, 2007
INVENTOR(S) : Aziz Fadli et al.

It is certified that error appears in the above-identified patent and that said Letters Patent is hereby corrected as shown below:

In claim 10, column 33, lines 3-4, "3-(methylsulphonylamino)pyrroline," should read --3-(methylsulphonylamino)pyrrolidine,--.

In claim 11, column 33, lines 10-11, "3-(methyl-sulphonylamino)pyrrolidine" should read --3-(methylsulphonylamino)pyrrolidine--.

In claim 13, column 33, line 16, "2,3,5,-triaminopyridine" should read --2,3,5-triaminopyridine--.

In claim 26, column 36, line 10, "as $R_3$," should read --as $R_1$,--.

In claim 27, column 36, line 37, "$NR_3R_4$radicals;" should read --$NR_3R_4$ radicals;--.

Signed and Sealed this

Twenty-ninth Day of May, 2007

JON W. DUDAS
*Director of the United States Patent and Trademark Office*